United States Patent
Yau et al.

(10) Patent No.: US 7,854,611 B2
(45) Date of Patent: Dec. 21, 2010

(54) METHOD OF GENERATING A DIGITAL SUPPLEMENTARY DEVICE FOR DENTAL IMPLANT PLANNING

(75) Inventors: Hong-Tzong Yau, Chiayi County (TW); Chuan-Chu Kuo, Chiayi County (TW); Jiun-Ren Chen, Yunlin County (TW); Fu-Chieh Hsiao, Chiayi (TW)

(73) Assignee: Pou Yu Biotechnology Co., Ltd., Chang Hwa Hsien (TW)

( * ) Notice: Subject to any disclaimer, the term of this patent is extended or adjusted under 35 U.S.C. 154(b) by 310 days.

(21) Appl. No.: 12/155,705

(22) Filed: Jun. 9, 2008

(65) Prior Publication Data

US 2009/0092946 A1  Apr. 9, 2009

(51) Int. Cl.
A61C 13/20 (2006.01)
(52) U.S. Cl. ........................................ 433/213; 433/75
(58) Field of Classification Search .............. 433/75, 433/76, 213, 215
See application file for complete search history.

(56) References Cited

U.S. PATENT DOCUMENTS

| | | | | |
|---|---|---|---|---|
| 5,842,858 A | * | 12/1998 | Truppe | 433/69 |
| 5,927,982 A | * | 7/1999 | Kruger | 433/215 |
| 5,967,777 A | * | 10/1999 | Klein et al. | 433/75 |
| 6,319,006 B1 | * | 11/2001 | Scherer et al. | 433/215 |
| 6,814,575 B2 | * | 11/2004 | Poirier | 433/75 |
| 2007/0190481 A1 | * | 8/2007 | Schmitt | 433/68 |
| 2009/0042167 A1 | * | 2/2009 | Van Der Zel | 433/215 |
| 2009/0162813 A1 | * | 6/2009 | Glor et al. | 433/196 |

FOREIGN PATENT DOCUMENTS

WO   WO 2007/009719   *   1/2007

* cited by examiner

*Primary Examiner*—Ralph A Lewis
(74) *Attorney, Agent, or Firm*—Bacon & Thomas, PLLC

(57) ABSTRACT

A method of generating a digital supplementary device for dental implantation by: preparing a mouth model based on the internal shape of the oral cavity of the patient; performing a 3D scan to obtain digital model of the mouth model, the digital model of the patient's oral cavity and the digital model of the tooth model; defining the digital models as the "positioning object," "the reference object" and the "attached positioning object"; obtaining characteristic points after joining the positioning object and the attached positioning object and positioning the positioning object and the reference object based on the characteristic points; and then outputting the attached positioning object with the positioning data obtained after positioning of the attached positioning object. The output thus obtained is the desired digital supplementary device for dental implant planning.

12 Claims, 6 Drawing Sheets

ND OF A DIGITAL SUPPLEMENTARY DEVICE FOR DENTAL IMPLANT PLANNING

BACKGROUND OF THE INVENTION

1. Field of the Invention

The present invention relates to dental implant techniques and more particularly, to a method of generating a digital supplementary device for dental implant planning

2. Description of the Related Art

Conventional dental implantation techniques commonly emphasize evaluation of bone quality while ignoring cross-bite quality. It is a normal concept to ordinary people skilled in the art that the most important thing is the consideration of the position of the implant fixture, and an angled abutment tooth can be used to make correction in case the axial biasing is over a predetermined range after implantation of the implant fixture.

The above method is not the best way. Although bone quality is important, ignoring bite quality results in many problems. If the implant fixture deviates from the cross-bite reference plane, the implant fixture will bear an axial force and a bending force during the biting between the upper teeth and the lower teeth or when the upper teeth and the lower teeth bite an object. An excessive bending force may destruct the bonding between the implant fixture and the alveolar bone, shortening the service life of the implant fixture, or resulting in bone integration failure a certain period after surgery.

Further, if the axial biasing of the implant fixture surpasses the correction range of the abutment after its implantation, the bite face of the loaded denture will deviate, loosing the bite function.

Therefore, the position, angle and axial direction of the implant fixture must be well planned before implantation. It is a workable choice to perform implantation planning via a computer-aided digital tooth model.

SUMMARY OF THE INVENTION

The present invention has been accomplished with the circumstances in view. It is one object of the present invention to provide a method of generating a digital supplementary device for dental implant planning that generates a digital tooth model supplementary device with the assistance of a computer-aided system, facilitating accurate dental implant planning and installation.

To achieve this and other objects of the present invention, the method of generating a digital supplementary device for dental implantation comprises the steps of: a) preparing a mouth model subject to the internal shape of the oral cavity of the patient; b) using a three-dimensional scanner to scan the mouth model so as to obtain a digital model and defining the digital model as a "positioning object," and then loading a digital tooth model of the missing tooth or teeth in the positioning object in the place where the tooth or teeth are missing and defining the digital tooth model as an "attached positioning object"; c) scanning the oral cavity of the patient by means of CT (computed tomography) scan to obtain a digital model and defining the digital model as a "reference object"; d) selecting multiple corresponding points of the positioning object and the reference object as characteristic points; e) overlapping the positioning object and the reference object by means of the characteristic points of the positioning object and the reference object to have the attached positioning object be positioned on the reference object; and f) obtaining a positioning data of the attached positioning object and outputting the attached positioning object and the positioning data to provide a digital supplementary device for dental implant planning.

DETAILED DESCRIPTION OF THE INVENTION

Figure 1:
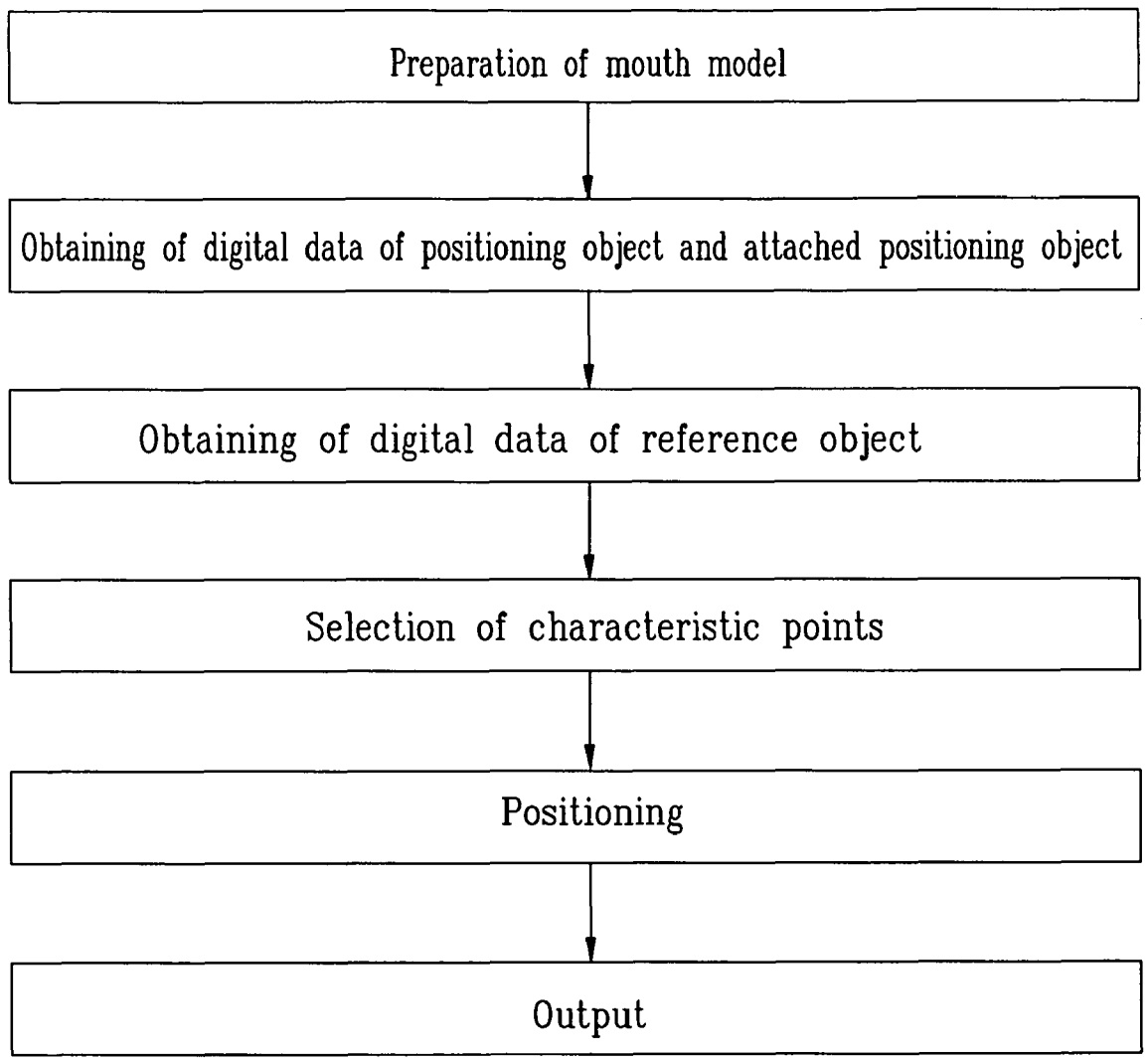
FIG. 1 is a flow chart of a method of generating a digital supplementary device for dental implant planning in accordance with a first embodiment of the present invention.
Figure 2:
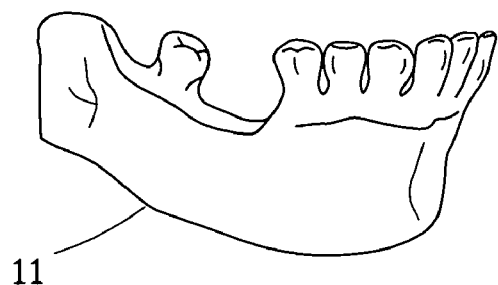
FIG. 2 is a schematic drawing showing a mouth model obtained according to the first embodiment of the present invention.
Figure 3:
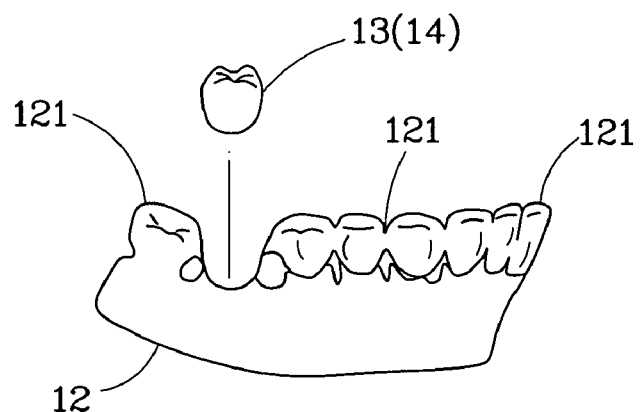
FIG. 3 is a schematic drawing showing the configuration of a positioning object obtained according to the first embodiment of the present invention.
Figure 4:
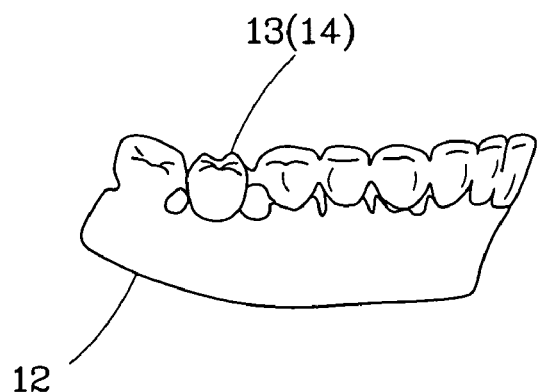
FIG. 4 corresponds to FIG. 3, showing the attached positioning object joined to the positioning object.
Figure 5:
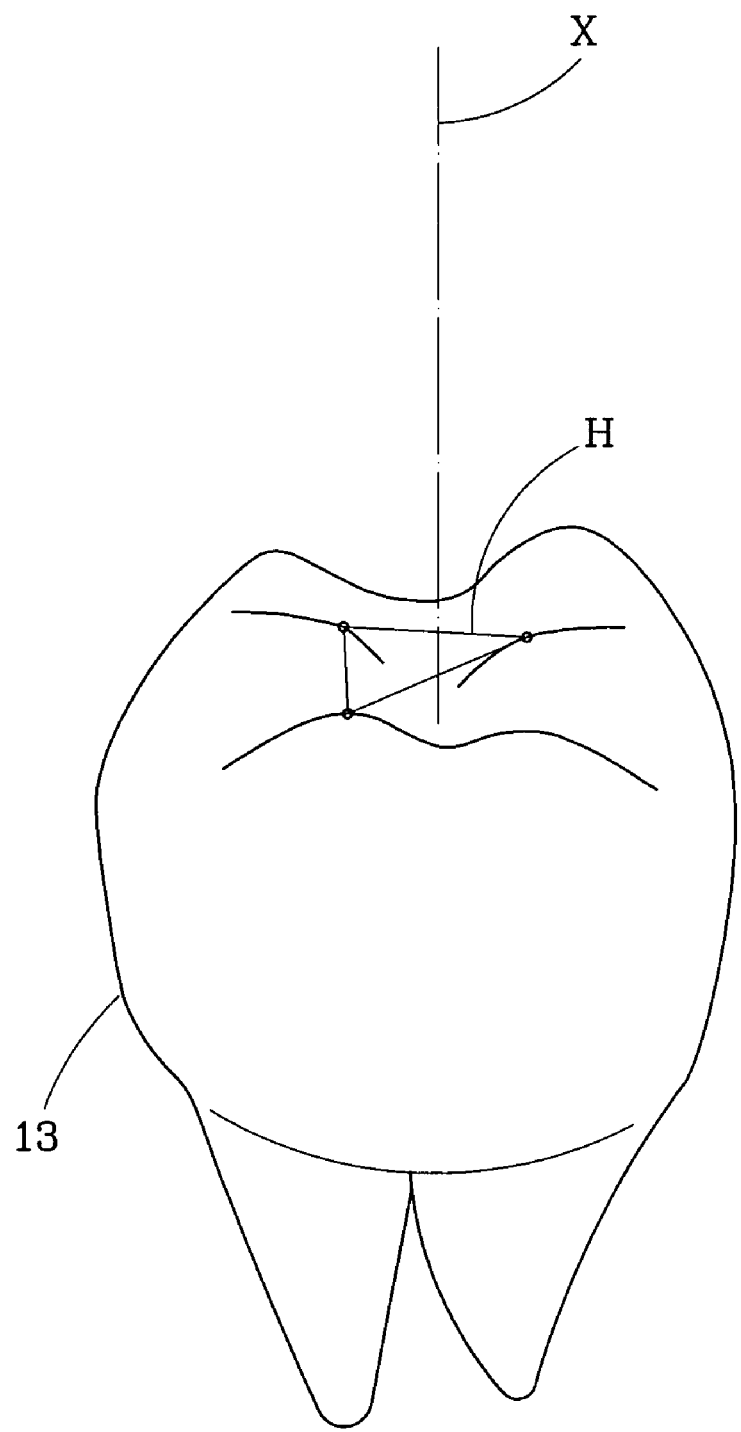
FIG. 5 is a schematic drawing showing the direction of the stress-bearing axis of the digital tooth model during bite according to the first embodiment of the present invention.
Figure 6:
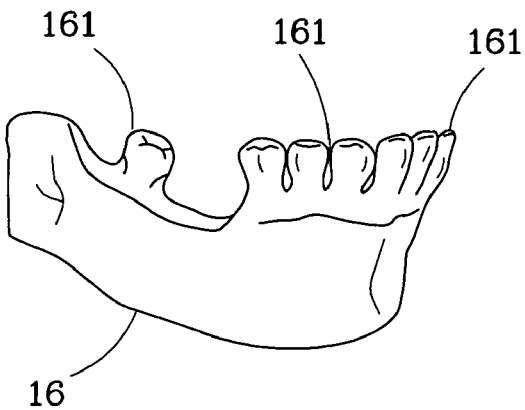
FIG. 6 is a schematic drawing showing the configuration of a reference object obtained according to the first embodiment of the present invention.
Figure 7:
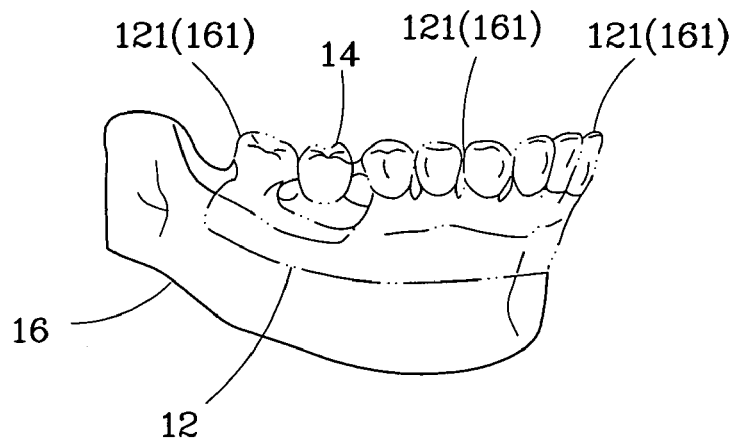
FIG. 7 corresponds to FIG. 6, showing the positioning status of the attached positioning object in the reference object according to the first embodiment of the present invention.
Figure 8:
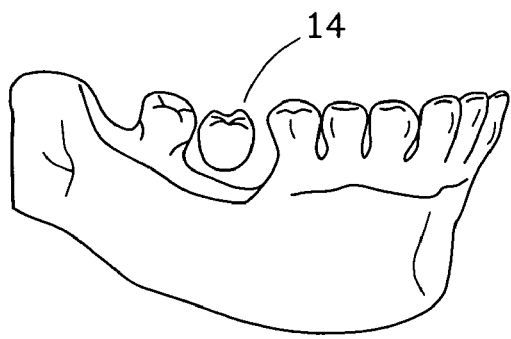
FIG. 8 is a schematic drawing showing the predicted surgical result after dental implantation according to the first embodiment of the present invention.
Figure 9:
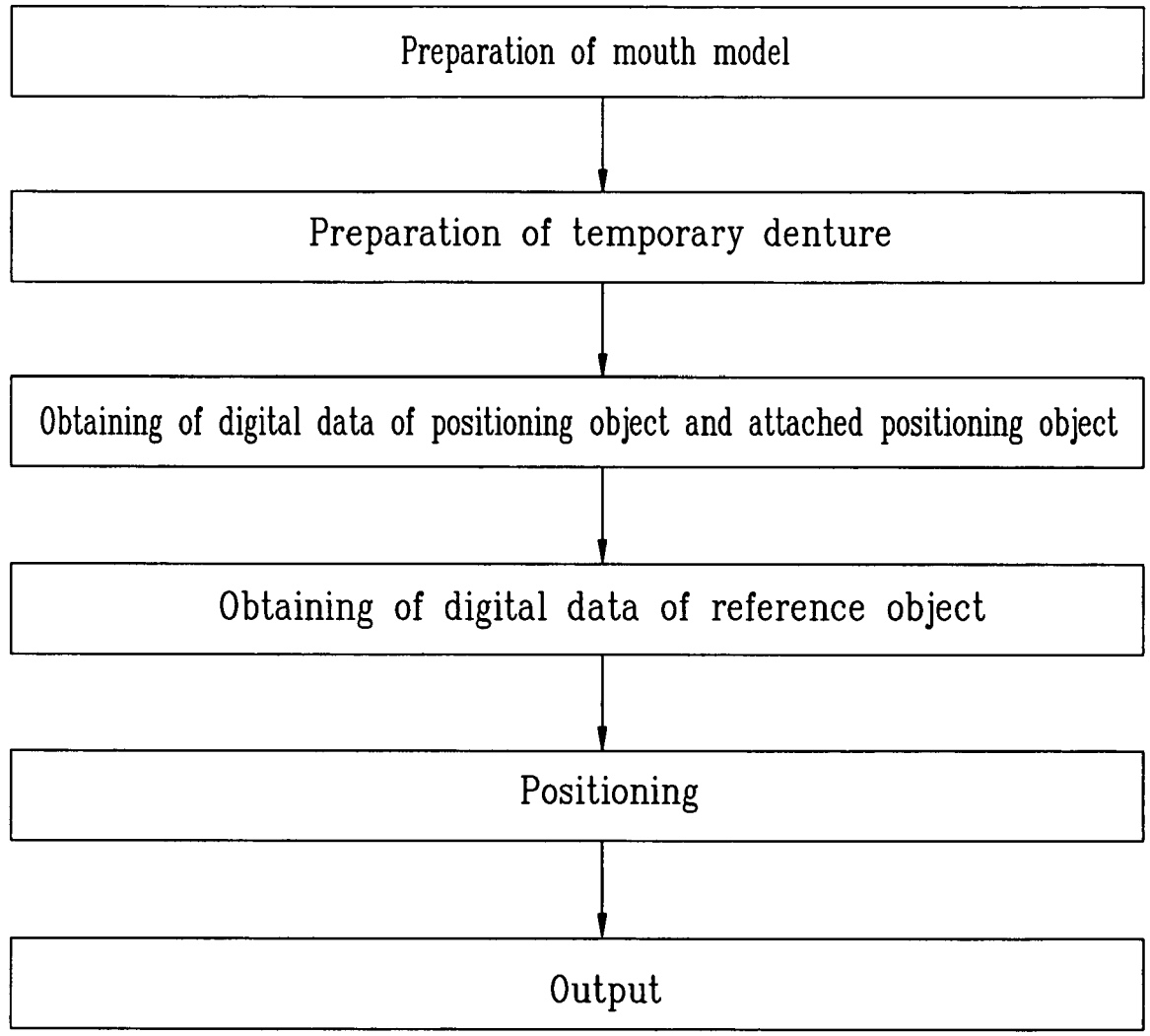
FIG. 9 is a flow chart of a method of generating a digital supplementary device for dental implant planning in accordance with a second embodiment of the present invention.
Figure 10:
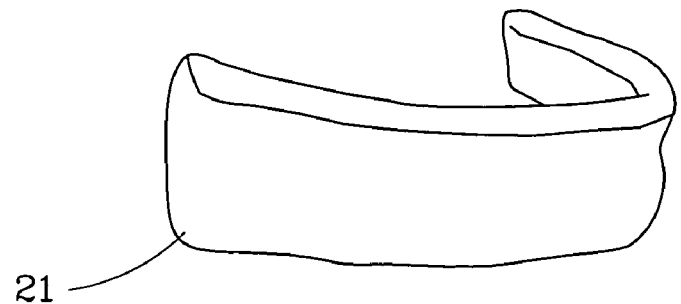
FIG. 10 is a schematic drawing showing a mouth model made based on the configuration of the oral cavity of the patient according to the second embodiment of the present invention.
Figure 11:
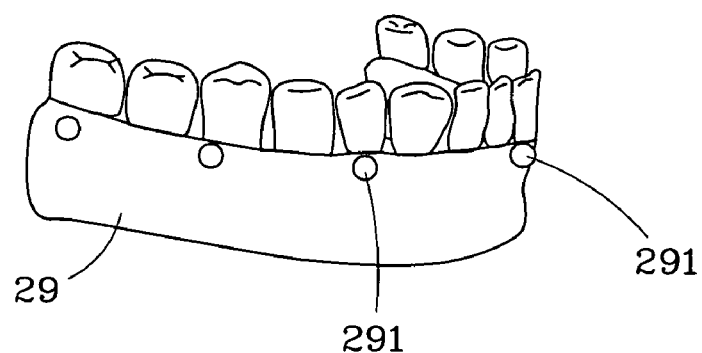
FIG. 11 is a schematic drawing a temporary denture made based on the configuration of the mouth model according to the second embodiment of the present invention.
Figure 12:
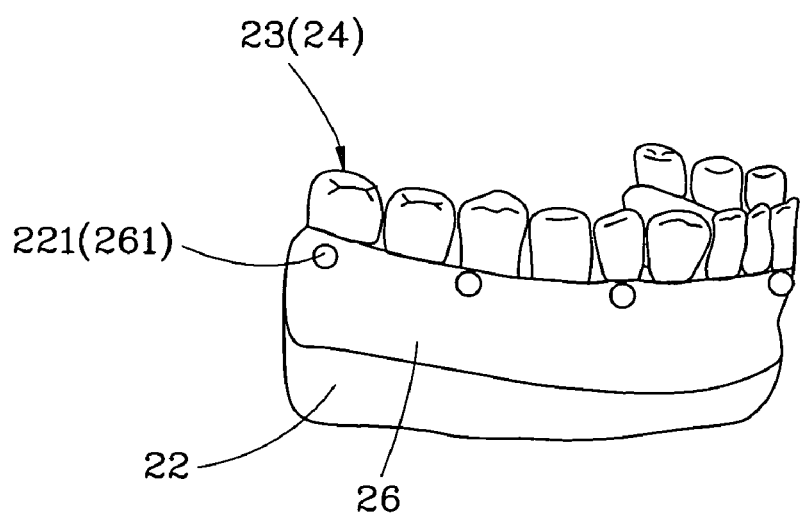
FIG. 12 is a schematic drawing showing a reference object positioned in the positioning object according to the second embodiment of the present invention.

Referring to FIG. 1, a method of generating a digital supplementary device for dental implant planning in accordance with a first embodiment of the present invention includes the steps of:

a) Preparation of mouth model: As shown in FIG. 2, copy the internal shape of the oral cavity of the patient to make a mouth model 11.

b) Obtaining of digital data of positioning object and attached positioning object: As shown in FIGS. 3 and 4, use a 3D scanner (not shown) to scan the mouth model 11 so as to obtain a digital model, which is defined as a "positioning object" 12, and then obtain a digital tooth model 13 from a database of standard tooth models (not shown) based on the configuration of the place where the tooth or teeth are missing, and then load the digital tooth model 13 in the aite where the tooth or teeth are missing, and the digital tooth model 13 is defined as an "attached positioning object" 14 after its loading. The attached positioning object 14 can be a digital tooth model scanned from a preparation tooth model (not shown) based on the configuration of the site of the missing tooth or teeth. Three cusp points are selected from the occlusal surface of the digital tooth model 13 to define an occlusal plane H, and then, a straight line X is defined such that it is based on the reference point of the recessed portion of the occlusal surface of the digital tooth model 13 and is extended perpendicularly to the occlusal surface of the digital tooth model 13, as shown in FIG. 5. The straight line X is the longitudinal axis of the digital tooth model 13 when biting. The standard tooth models database is of the known art commonly seen in commercial dental design software. Therefore, no further description or illustration is necessary.

c) Obtaining of digital data of reference object: Scan the oral cavity of the patient by means of CT (computed tomography) scan to obtain a digital model that is defined as a "reference object" 16, as shown in FIG. 6.

d) Selecting of characteristic points: Select multiple corresponding points of the positioning object 12 and the reference object 16 as characteristic points 121 and 161. The characteristic points 121 and 161 each can be selected from the cusps or the recessed portions of the occlusal surface of a specific tooth or the contact point between two adjacent teeth or a combination of these, as shown in FIGS. 3 and 6.

e) Positioning: As shown in FIG. 7, overlap the characteristic points 121 and 161 to join the positioning object 12 and the reference object 16, i.e., overlap the characteristic points 121 of the positioning object 12 on the characteristic points 161 of the reference object 16 to position the positioning object 12 on the reference object 16. At this time, the attached positioning object 14 is positioned on the reference object 16, and therefore the positioning data of the attached positioning object 14 is obtained, as shown in FIG. 8. During execution, the overlap positioning action is performed by a computer.

f) Output: The positioning data of the attached positioning object 14 thus obtained (not shown) is outputted with the attached positioning object 14 itself, and the output is a digital supplementary device for dental implant planning. The positioning data includes at least the coordinates of the attached positioning object 14 and its stress-bearing axis.

By means of the aforesaid procedure, a digital supplementary device for dental implant planning is obtained before dental implantation. The digital supplementary device comprises the attached positioning object 14 (i.e., the digital model of the digital tooth model 13) and the positioning data (coordinates, force-bearing axis, etc.) of the attached positioning object 14. This digital supplementary device for dental implant planning helps the dentist know the cross bite of the patient's teeth and the angle and position of the implant fixture before dental implantation, improving dental implantation accuracy. Further, by means of displaying the digital supplementary device on the display screen of a computer system, the dentist and the patient can predict the result before the start of surgery. FIG. 8 illustrates the predicted surgical result.

FIGS. 9~12 show the generation of a digital supplementary device for dental implant planning in accordance with a second embodiment of the present invention. As illustrated, the method according to this second embodiment includes the steps of:

a) Preparation of mouth model: As shown in FIG. 2, copy the internal shape of the oral cavity of the patient to make a mouth model 21.

b) Preparation of temporary denture: Prepare a temporary denture 29 based on the configuration of the mouth model 21, and select multiple specific objects on the temporary denture 29 as characteristic points 291.

c) Obtaining of digital data of positioning object and attached positioning object: Use a 3D scanner (not shown) to scan the mouth model 21 so as to obtain a digital model, which is defined as a "positioning object" 22 that has multiple characteristic points 221. Alternatively, the temporary denture 29 can be capped on the mouth model 21 before performing a 3D scan, and the characteristic points 291 of the temporary denture 29 form the characteristic points 221 of the positioning object 22 after performance of a 3D scan to obtain the digital model. Thereafter, obtain a digital tooth model 23 from a database of standard tooth models (not shown) based on the site where the tooth or teeth are missing and then load the digital tooth model 23 in the place where the tooth or teeth are missing, and the digital tooth model 23 is defined as an "attached positioning object" 24 after its loading. The attached positioning object 24 can be a digital tooth model scanned from a preparation tooth model (not shown) based on the configuration of the site of the missing tooth or teeth. Three cusp points are selected from the occlusal surface of the digital tooth model 23 to define an occlusal plane H, and then a straight line X is defined such that it is based on the reference point of the recessed portion of the occlusal surface of the digital tooth model 23 and is extended perpendicularly to the occlusal surface of the digital tooth model 23. The straight line X is the longitudinal axis of the digital tooth model 23 when biting. The database of the standard tooth models is of the known art commonly seen in commercial dental design software. Therefore, no further description or illustration is necessary.

d) Obtaining of digital data of reference object: Scan the oral cavity of the patient by means of CT (computed tomography) scan to obtain a digital model that is defined as a "reference object" 16 having multiple characteristic points 261.

e) Positioning: Overlap the characteristic points 221 and 261 to join the positioning object 22 and the reference object 26, i.e., overlap the characteristic points 221 of the positioning object 22 on the characteristic points 261 of the reference object 26 to position the positioning object 22 on the reference object 26. At this time, the attached positioning object 24 is positioned on the reference object 26, and therefore the positioning data of the attached positioning object 24 is obtained. During execution, the overlap positioning action is performed by a computer.

f) Output: The positioning data of the attached positioning object 24 thus obtained (not shown) is outputted with the attached positioning object 24 itself, and the output is a digital supplementary device for dental implant planning. The positioning data includes at least the coordinates of the attached positioning object 44 and its force-bearing axis.

This second embodiment is substantially similar to the aforesaid first embodiment with the exception of the extra temporary denture 29. This embodiment is practical for a dental implant planning to a patient whose teeth are all absent.

As stated above, the invention generates a digital supplementary device for dental implant planning with the assistance of a computer-aided system, facilitating accurate dental implant planning and installation.

Although particular embodiments of the invention have been described in detail for purposes of illustration, various modifications and enhancements may be made without departing from the spirit and scope of the invention. Accordingly, the invention is not to be limited except as by the appended claims

What is claimed is:

1. A method of generating a digital supplementary device for dental implantation, comprising the steps of:

a) preparing a mouth model based on the internal shape of the oral cavity of the patient;

b) using a 3D scanner to scan said mouth model so as to obtain a digital model and defining the digital model as a positioning object, and then loading a digital tooth model of the missing tooth or teeth in said positioning object in the place where the tooth or teeth are missing and defining said digital tooth model as an attached positioning object;

c) scanning the oral cavity of the patient by means of CT (computed tomography) scan to obtain a digital model and defining the digital model as a reference object;

d) selecting multiple corresponding points of said positioning object and said reference object as characteristic points;

e) overlapping said positioning object and said reference object by means of the characteristic points of said positioning object and said reference object to have said attached positioning object be positioned on said reference object; and f) obtaining positioning data of said attached positioning object and outputting said attached positioning object and said positioning data to provide a digital supplementary device for dental implant planning, wherein the positioning data obtained during step f) comprises at least the coordinates and stress-bearing axis of said attached positioning object, and wherein during step b), three cusp points are selected from the occlusal surface of said digital tooth model to define an occlusal plane, and then a straight line is defined such that it is based on the reference point of the recessed portion of the occlusal surface of said digital tooth model and is extended perpendicularly to the occlusal surface of said digital tooth model, where the straight line is the stress-bearing axis of said digital tooth model.

2. The method of generating a digital supplementary device for dental implantation as claimed in claim 1, wherein said positioning object and said reference object are overlapped during step e) by means of positioning said positioning object on said reference object.

3. The method of generating a digital supplementary device for dental implantation as claimed in claim 1, wherein during step d), said characteristic points are selected from the cusps or the recessed portions of the occlusal surfaces or the contact points between two adjacent teeth or from a combination of points on these areas.

4. The method of generating a digital supplementary device for dental implantation as claimed in claim 1, wherein during step b), said attached positioning object is a digital tooth model obtained from a database of standard tooth models and is based on the configuration of the site where the tooth or teeth are missing.

5. The method of generating a digital supplementary device for dental implantation as claimed in claim 1, wherein during step b), said attached positioning object is a digital tooth model scanned from a preparation tooth model based on the configuration of the site where the tooth or teeth are missing.

6. A method of generating a digital supplementary device for dental implantation, comprising the steps of:

a) preparing a mouth model based on the internal shape of the oral cavity of the patient;

b) preparing a temporary denture based on the configuration of said mouth model and selecting multiple specific objects on said temporary denture as characteristic points;

c) scanning said temporary denture by means of 3D scanner to obtain a digital model having multiple characteristic points and defining the digital model as a positioning object, and then loading a digital tooth model in the place where the tooth is absent and defining the digital tooth model as an attached positioning object;

d) putting said temporary denture on the patient and scanning the oral cavity of the patient by means of CT (computed tomography) scan to obtain a digital model and then defining the digital model as a reference object that has multiple characteristic points;

e) overlapping said positioning object and said reference object by means of the characteristic points of said positioning object and said reference object to have said attached positioning object be positioned on said reference object; and f) obtaining a positioning data of said attached positioning object and outputting said attached positioning object and said positioning data to provide a digital supplementary device for dental implant planning.

7. The method of generating a digital supplementary device for dental implantation as claimed in claim 6, wherein said positioning object and said reference object are overlapped during step e) by means of positioning said positioning object on said reference object.

8. The method of generating a digital supplementary device for dental implantation as claimed in claim 6, wherein the positioning data obtained during step f) comprises at least the coordinates and stress-bearing axis of said attached positioning object.

9. The method of generating a digital supplementary device for dental implantation as claimed in claim 8, wherein during step b), three cusp points are selected from the occlusal surface of said digital tooth model to define an occlusal plane, and then a straight line is defined such that it is based on the reference point of the recessed portion of the occlusal surface of said digital tooth model and is extended perpendicularly to the occlusal surface of said digital tooth model, and the straight line is the stress-bearing axis of said digital tooth model.

10. The method of generating a digital supplementary device for dental implantation as claimed in claim 6, wherein during step c), said digital tooth model is obtained from a standard database of tooth models and is based on the configuration of the site where the tooth or teeth are missing.

11. The method of generating a digital supplementary device for dental implantation as claimed in claim 6, wherein during step c), said attached positioning object is a digital tooth model scanned from a preparation tooth model based on the configuration of the site where the tooth or teeth are missing.

12. The method of generating a digital supplementary device for dental implantation as claimed in claim 6, wherein during step c), said temporary denture is capped on said mouth model before scanning.

* * * * *